United States Patent
Ungerstedt

[19]

[11] Patent Number: 5,925,018
[45] Date of Patent: Jul. 20, 1999

[54] INFUSION AND MICRODIALYSIS PUMP

[75] Inventor: Urban Ungerstedt, Lidingö, Sweden

[73] Assignee: CMA/Microdialysis AB, Solna, Sweden

[21] Appl. No.: 08/817,121

[22] PCT Filed: Nov. 13, 1995

[86] PCT No.: PCT/SE95/01344

§ 371 Date: Apr. 8, 1997

§ 102(e) Date: Apr. 8, 1997

[87] PCT Pub. No.: WO96/14893

PCT Pub. Date: May 23, 1996

[30] Foreign Application Priority Data

Nov. 14, 1994 [SE] Sweden .................................. 9403910

[51] Int. Cl.[6] .................................................. A61M 37/00
[52] U.S. Cl. ........................... 604/155; 604/154; 604/131
[58] Field of Search .................................... 604/131, 154, 604/155, 245, 134, 135; 128/DIG. 1, DIG. 12

[56] References Cited

U.S. PATENT DOCUMENTS

| 3,701,345 | 10/1972 | Heilman et al. ............... 604/155 X |
| 3,812,843 | 5/1974 | Wooten et al. ............... 604/155 X |
| 3,858,581 | 1/1975 | Kamen ....................... 604/155 |
| 4,191,187 | 3/1980 | Wright ....................... 604/155 |
| 4,424,720 | 1/1984 | Bucchanieri ............... 604/155 X |
| 4,435,173 | 3/1984 | Siposs et al. ............. 604/155 |
| 4,529,401 | 7/1985 | Leslie et al. ............. 604/131 |
| 4,544,369 | 10/1985 | Skakoon et al. ........... 604/155 |
| 4,562,751 | 1/1986 | Nason et al. . |
| 4,681,566 | 7/1987 | Fenton, Jr. et al. ...... 604/135 |
| 4,731,058 | 3/1988 | Doan ....................... 604/155 |
| 5,505,709 | 4/1996 | Funderburk et al. ....... 604/155 |
| 5,647,853 | 7/1997 | Feldmann et al. .......... 604/155 |

FOREIGN PATENT DOCUMENTS

| 0 285 403 | 10/1988 | European Pat. Off. . |
| 0 388 102 | 9/1990 | European Pat. Off. . |

OTHER PUBLICATIONS

Cordis Corporation, Cat. No. 404–100, 404–102, Lymphography Injector, 1972.

Primary Examiner—Richard J. Apley
Assistant Examiner—Justine R. Yu
Attorney, Agent, or Firm—Young & Thompson

[57] ABSTRACT

An infusion and microdialysis pump comprises a casing (100, 200) and an insertable cylinder and plunger (300) of the injection syringe type. Seated on the plunger rod is a runner element (4) which runs on a motor-driven screw (3), thereby to cause the plunger to dispense fluid.

3 Claims, 2 Drawing Sheets

INFUSION AND MICRODIALYSIS PUMP

FIELD OF THE INVENTION

The present invention relates to an infusion and microdialysis pump of the kind in which a plunger pump in the form of an injection syringe can be fitted in a casing, which includes a motor and drive means connected thereto, wherein the plunger can be moved in the pump chamber and therewith gradually press-out fluid for infusion and microdialysis purposes.

BACKGROUND OF THE INVENTION

Such devices are known and commercially available. Equipped with present-day electronic control devices, these devices are able to perform a large number of tasks, such as to inject into patients appropriately measured quantities of insulin or morphine, as required by the patient. Such arrangement are sufficiently small to be connected comfortably to the patient or carried comfortably thereby, and can therewith be used for microdialysis.

The price paid for the smallness and ease of handling of such devices, however, is that it is difficult and troublesome to fit the actual syringe. This difficulty can be tolerated, if necessary, when the device is filled and put in order clinically or polyclinically by experienced and trained personnel, but proves troublesome when a patient or relative has to fill and put the device in order in his or her own home. An object of the present invention is therefore to provide an infusion and microdialysis pump of the kind defined in the introduction where charging and insertion of a syringe into the casing can be effected without requiring particular expertise or skill.

SUMMARY OF THE INVENTION

In accordance with the invention, a syringe, preferably a disposable syringe, shall be capable of being fitted easily into a casing and connected to a motor-driven screw and kept in place by means of a lid, preferably a hinged lid, placed over the syringe. This will ensure that the syringe pusher will come into positive thread engagement with the screw, irrespective of the volume of fluid contained in the syringe. However, the strength of this thread engagement is not sufficiently great to prevent screw engagement being released by virtue of the elasticity of the runner should the screw be rotated to an extent greater than the length of stroke available in the syringe. The runner is preferably made of plastic, and can be made integral with the outer end of the pump plunger or may have the form of a separate component which can be fastened to said end.

The syringe has provided adjacent its outlet orifice a recess or like means which accommodates a bead in the injection position of the casing. When fitting the syringe into the casing, the syringe is placed with the recess against the bead, wherewith the rear part of the syringe rests inclined against a spring device. As a pivotal lid is then swung down over the syringe, the syringe will be moved around the bead to a position in which it lies parallel with the screw under the action of the spring device, so that the rearwardly seated runner on the pusher will be pressed down into a running position on the screw. The two legs of the runner press against the sides of the screw, and the serrated or grooved side of the runner will engage the screw over six-thread lengths, for instance.

In the case of a right-hand screw, it is suitable for the left-hand side of the runner to be in engagement with the screw, as seen in the outwardly projecting direction of the syringe, which causes the transverse forces that are exerted as the screw rotates and which are due to the inclination of the grooves and the threads will tend to cause the syringe to be drawn inwards and thus not outwards towards the lid.

The drive arrangement is designed as a casing for accommodating the pump chamber and a plunger, with a threaded screw connected to an electric, battery-operated motor, wherein the plunger rod extends beyond the pump chamber and carries a forked device which is open at right angles to the plunger axis and which can be caused to clamp resiliently around the screw, wherein at least one of the inwardly facing sides of the fork means has a grooved pattern whose periodicity coincides generally with the pitch of the screw and which is inclined in relation to the direction of plunger movement, such as to coincide with the slope of the screw threads on that side thereof against which the inwardly grooved side of the fork means resiliently abuts. It is preferred that only one side of the fork means is grooved, since the function is then retained even with less accurate centering between screw and fork means. The fork means is preferably made of plastic, for instance Delrin. The screw is preferably made of metal, and even more preferably of steel.

BRIEF DESCRIPTION OF THE DRAWINGS

The invention will now be described in more detail with reference to a non-limiting embodiment thereof and also with reference to the accompanying drawings.

DETAILED DESCRIPTION OF THE DRAWINGS

Figure 1:
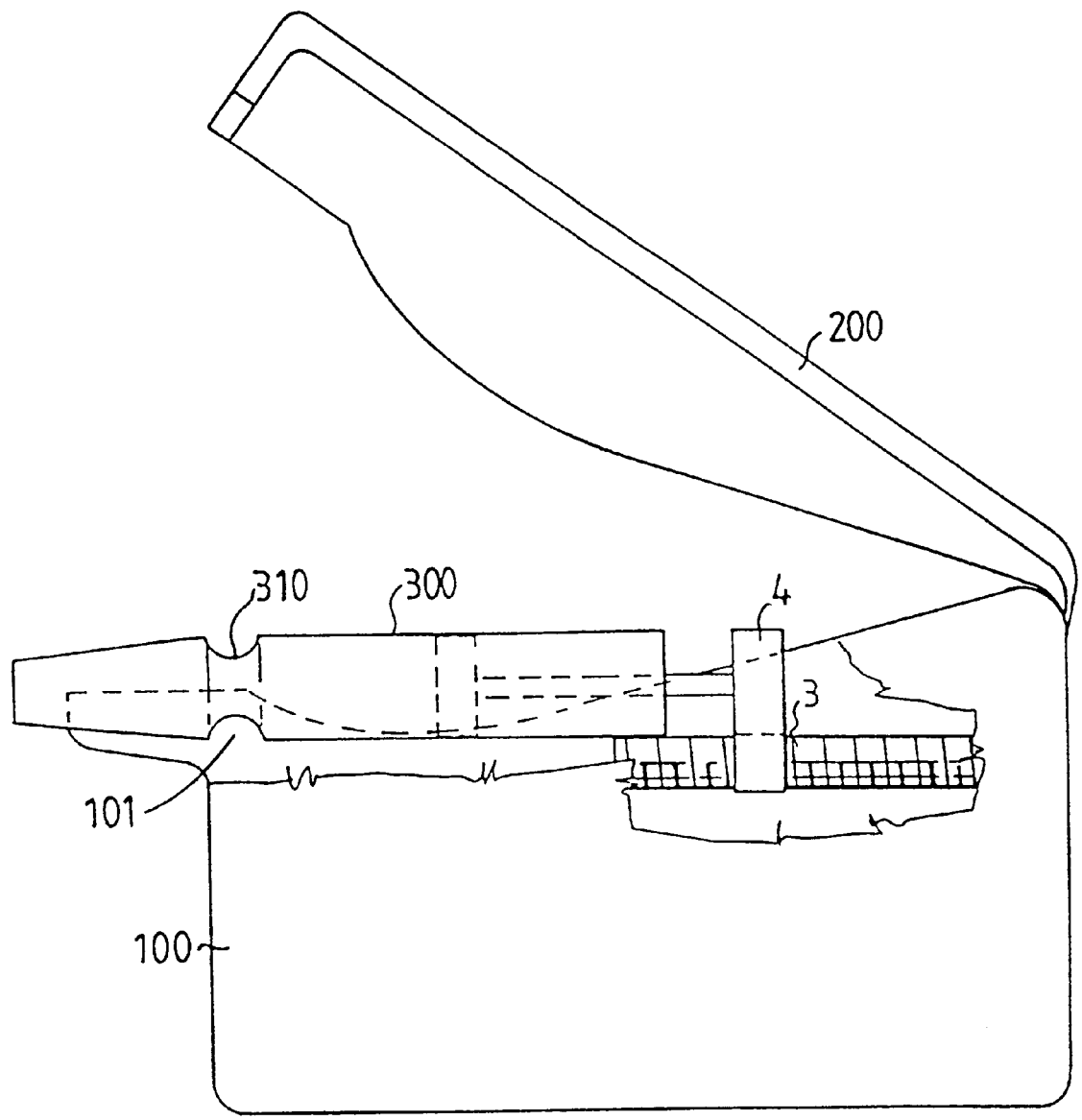
FIG. 1 illustrates schematically and partly in cross section a pump and an inserted syringe inserted.

Shown very schematically in FIG. 1 is a casing 100 which has a pivotal lid 200 and in which a syringe 300 is inserted and firmly held therein the medium of a groove 310 cooperating with a bead 101. As will be described in more detail below, the plunger of the syringe can be moved by means of the screw indicated in the Figure.

Figure 2:
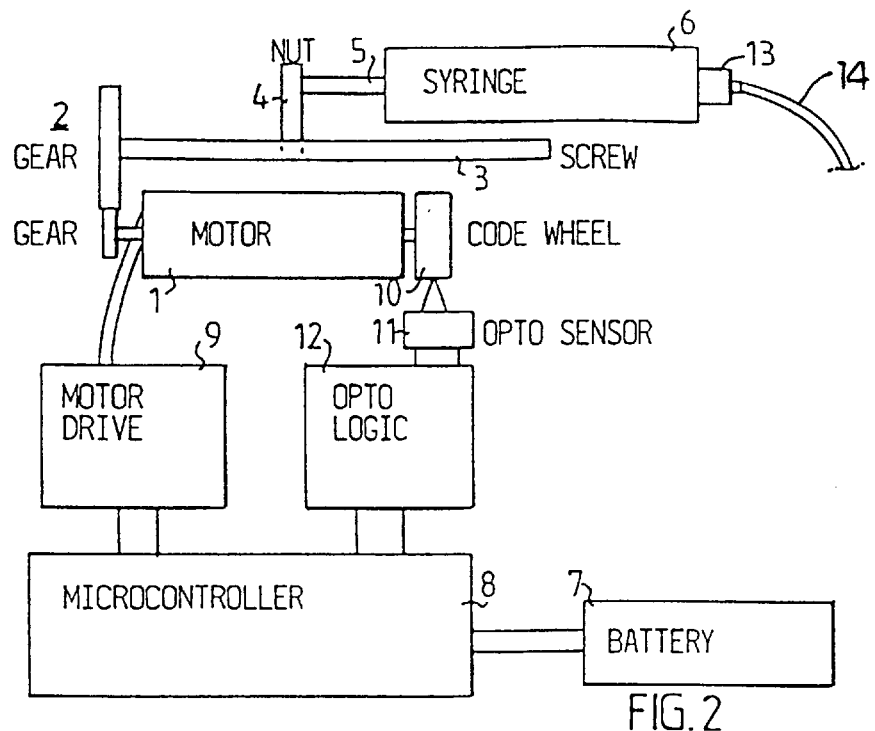
FIG. 2 is a block schematic of a microdialysis pump.

The principle illustration in FIG. 2 shows the active components of a microdialysis pump, and a drive motor 1 which drives a screw 3 through the medium of a gear 2. The screw is straddled by an open nut 4, as described in more detail below, which is fastened to (or made integral with) the plunger rod 5 of a pump corresponding to a syringe or the like 6. The power source has the form of a battery which is controlled by a microcontroller 8 so as to deliver electric current to the motor 1, via a motor drive unit 9. The motor has a through-extending shaft and carries on the end thereof distal from the transmission gearing a code wheel 10 provided with dark and light stripes (not shown) which are sensed by an opto-sensor 11 (light source and light sensor in combination), which signals rotation of the motor to the microcontroller 8 via an opto-logic means.

Figure 3:
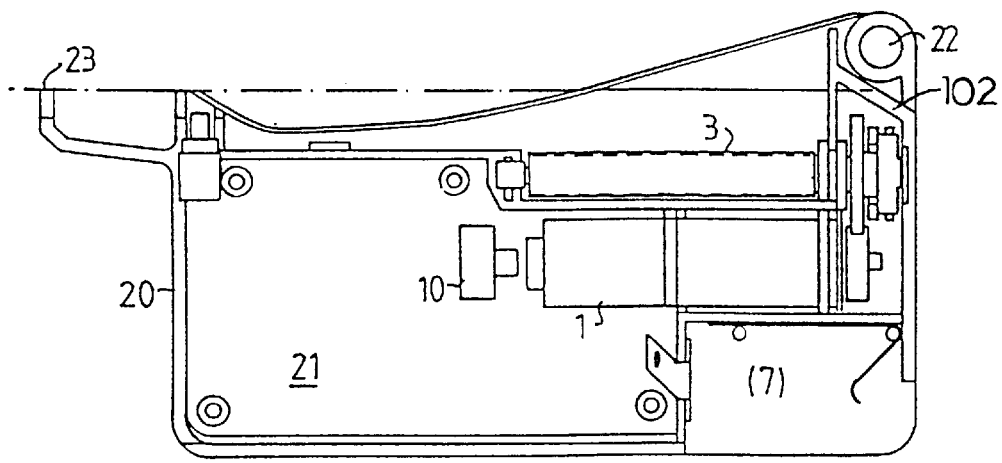
FIG. 3 is a sectional view of a casing with drive means for housing a pump chamber of the injection syringe kind and corresponding to a design illustrated in FIG. 2.

As will be seen from the cut-away view shown in FIG. 3, the motor 1, the code wheel 10, the gearing and the screw 3, the spring device 102 and the battery (7) are all mounted in a housing 20. Remaining components are mounted on the circuit card. Although not shown, an upper part is pivotally mounted at upper end 22, wherein a disposable injection syringe provided with a "straddle nut" 4 can be fitted and clamped beneath the lid with the outlet end 13 of the syringe lying in an opening 23 and the plunger rod connected for trans-latory movement upon rotation of the screw 3. A dispensing line 14 is conveniently connected to the outlet end 13.

Figure 5:
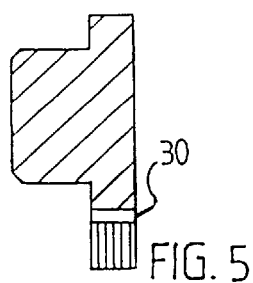
FIG. 5 is a cross sectional view taken on the line V—V in FIG. 4.
Figure 4:
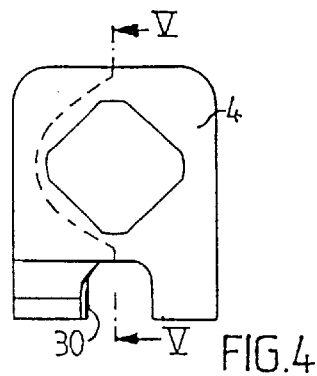
FIG. 4 illustrates a running nut which is intended to be fitted to the plunger rod of an injection syringe.

This simple arrangement is made possible by using a nut 4, shown in more detail in FIGS. 4 and 5, which includes a U-shaped recess whose one U-leg has a screw-thread 30 cut thereon, wherein the distance between the legs is adapted to the screw-thread of the screw 3.

In the case of one embodiment, the screw measures M5×0.5 in accordance with SMS 1701, and the distance between the U-legs prior to cutting the thread is 4.5 mm. The straight cut threads 30 on the U-leg suitably define an angle of 1.95° to the cross direction of the nut. The nut may suitably be made of a plastic material, such as Delrin.

In the illustrated embodiment, the motor 1 is built together with a conventional gearbox (not shown) so as to obtain a total ratio of 108:1 together with the gearing 2. When using a conventional disposable syringe (3 ml), the syringe will dispense 0.5 ml of fluid with each rotation of the motor. The screw has a pitch of 0.5 mm and $\frac{1}{108}$ of a full rotation of the motor will thus result in a translation of about 4 $\mu$m. Since the motor always rotates in one and the same direction, any gaps that are present will have only a negligible effect.

When using a motor designed for a nominal 12 V, it is possible to obtain a suitable feed speed with a 4 V battery, wherein one revolution of the motor will take about one-tenth of a second. When the device is used intermittently and the motor has a speed of one revolution per minute, battery consumption will be so low as to enable a battery to last for fifteen calendar days. However, the investigation period is seldom longer than three to five calendar days.

When inserting a microdialysis catheter, it is necessary to undertake a filling and flushing period, which, e.g., may involve the discharge of 100 $\mu$l of fluid at a rate of 15 $\mu$l per minute and thus with one motor revolution each other second. Furthermore, all transmission gaps and clearances will be leveled out during this time period. In the following sampling period, fluid is discharged at one revolution per minute, thus in an intermittent quantity of 0.5 $\mu$l.

This example relates to a microdialysis catheter having an effective volume of 0.5 $\mu$l or negligibly thereabove. When other microdialysis catheters are used, the pump must be adapted accordingly, since the concept is to replace the fluid in the active part of the catheter on each occasion, with no surplus fluid being pressed through and therewith diluting the sample solution. It can be mentioned that individual sample volumes are normally collected during successive time periods, for instance time periods of 15 min., 30 min. or 1 hr., depending on the speed at which, for instance, metabolic developments change such as changes in the sugar values of diabetics or other changes. In other cases, the pump may be used to deliver substances to a patient, and this example should not therefore be considered all-inclusive.

It will be noted that the arrangement shown in the cut-away view of FIGS. 1 and 3 is roughly to scale, and it will therefore be readily seen that the arrangement can be carried easily by a patient, and that the patient will experience no appreciable discomfort and that said arrangement can be used in any situation whatsoever and even when taking working samples. The person skilled in this art will understand that the entire arrangement can be attached to the body of the patient with the aid of a strap or with the aid of adhesive tape.

The person skilled in this art will understand that the use of the device to deliver liquids and fluids to patients is highly versatile, in hospitals, polyclinics and in the home.

I claim:

1. In an infusion and microdialysis pump comprising:

a casing;

support means supporting a syringe having a plunger and a pump chamber terminating in an outlet orifice, wherein a forward part of the pump chamber is attachable to the casing and has a dispensing line projecting from the casing;

an electric motor fitted in the casing;

a reduction gear connected to the motor;

a threaded screw coupled to an output shaft of the reduction gear; and a pusher means structured and arranged to move along the screw as the screw rotates, and to move the plunger in a longitudinal direction in the pump chamber;

the improvement wherein the pusher means is integral with the plunger and includes a runner adapted to be placed onto the screw, said runner including a surface that has grooves complementary to the thread of the screw;

said casing having a pivotal lid which, when opened, exposes at one end of said casing a semi-circular head for accommodating a recess in the pump chamber close to the outlet orifice of the chamber;

said casing comprising a spring means, which when the syringe is inserted into the casing holds the syringe positioned obliquely with its rear end slightly raised, wherein when the pivotal lid is lowered, the lid functions to press down the rear end of the syringe against the force of the spring means and therewith press the runner into a running position on the screw.

2. A pump according to claim 1, wherein when the syringe is inserted in the casing, the screw is disposed along a line that extends parallel with said longitudinal direction, and is offset in relation to a center line of the plunger.

3. A pump according to claim 1, wherein the runner includes two mutually facing, generally flat and mutually parallel surfaces, a first surface having ridges and troughs with a frequency which corresponds to the pitch of the thread of the screw, and an inclination which corresponds to a tangential direction of the thread of the screw, whereas the other surface lacks ridges and troughs.

\* \* \* \* \*